United States Patent [19]

Nohara et al.

[11] 4,151,180

[45] Apr. 24, 1979

[54] CHROMONE DERIVATIVES

[75] Inventors: Akira Nohara, Kyoto; Tomonobu Umetani; Yasushi Sanno, both of Osaka, all of Japan

[73] Assignee: Takeda Chemical Industries, Ltd., Japan

[21] Appl. No.: 524,939

[22] Filed: Nov. 18, 1974

Related U.S. Application Data

[62] Division of Ser. No. 349,848, Apr. 10, 1973, Pat. No. 3,896,114.

[30] Foreign Application Priority Data

Apr. 12, 1972 [JP] Japan ............................... 48-37235

[51] Int. Cl.$^2$ .......................................... C07D 311/22
[52] U.S. Cl. ................................ 260/345.2; 424/283
[58] Field of Search ....................................... 260/345.2

[56] References Cited

U.S. PATENT DOCUMENTS

| 3,853,921 | 12/1974 | Klutchko et al. | 260/345.2 |
| 3,862,143 | 1/1975 | Klutchko et al. | 260/345.2 |
| 3,872,108 | 3/1975 | Nohara et al. | 260/345.2 |

*Primary Examiner*—John M. Ford
*Attorney, Agent, or Firm*—Wenderoth, Lind & Ponack

[57] ABSTRACT

The present invention relates to novel chromone derivatives, which are shown by the following general formula

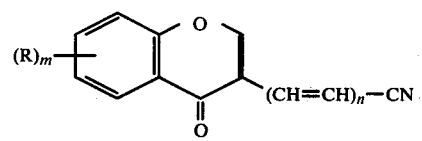

wherein n is 0 or 1, m is 0, 1 or 2 when each of R's represents halogen, nitro, straight or branched alkyl having 1 to 6 carbon atoms, cyclic alkyl having 3 to 6 carbon atoms or butadienylene (—CH=CH—CH=CH—) which forms a benzene ring with any two adjacent carbon atoms at positions 5, 6, 7 and 8, —COOR', wherein R' is hydrogen, lower alkyl, aralkyl, carboxamide which may be unsubstituted or substituted by at least one lower alkyl or aralkyl, or amino group which may be unsubstituted or substituted by R'CO—, wherein R' is a straight or branched chain alkyl or aryl, or lower alkyl, aralkyl or aryl, m is 0 or 1 when each of R's represents hydroxy, lower alkoxy or R'COO—, wherein R' is a straight or branched chain alkyl or aryl. The novel derivatives are useful as intermediates for chromones having effective anti-allergic action.

10 Claims, No Drawings

CHROMONE DERIVATIVES

This is a divisional of Ser. No. 349,848, filed Apr. 10, 1973, now U.S. Pat. No. 3,896,114.

The present invention relates also to a process for the production of these chromone derivatives.

Hitherto, there have been known many kinds of antihistamine agents, and some of them have been put into practical use. However, aforesaid known anti-histamine agents are not very satisfactory in view of one or more of such drawbacks as showing rather low anti-allergic activity and rather high toxicity and causing side effects (e.g. sedation, cardiac stimulation and headache) upon long-term administration.

Moreover, most of the known anti-histamine agents show only antagonism towards histamine released or produced in a living body and, thus, they are not satisfactory as a medicine for treating allergic disease which is caused by other allergy mediating substances, e.g. SRSA (Slow Reacting Substance of Anaphylaxis) than histamine.

The inhibition of the secretion of chemical mediators, such as SRSA and histamine, is very effective for the treatment of allergic disease, e.g. bronchial asthma. Hithertofore, however, no one has succeeded in synthesizing any compound in compliance with this purpose, at least from a practical or an industrial point of view.

Under these circumstances, present inventors have made extensive studies and succeeded in synthesizing specific new chromone derivatives (I) defined below, which have never previously been synthesized.

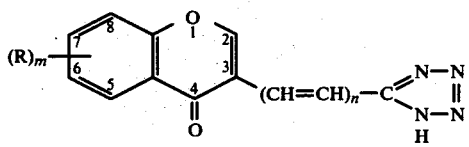

Moreover, the present inventors have also unexpectedly found that these compounds have a very strong action in preventing the secretion of SRSA and histamine from the cells of a living body, and they also show quite a low toxicity; furthermore, they show the above actions effectively even upon oral administration.

In view of these characteristics, the chromone derivatives of formula I can be used as an effective medicine for preventing and/or treating allergic diseases, especially bronchial asthma and rhinitis, by means of oral administration.

In the general formula (I), the alkyl group represented by the symbol R may be any of straight, branched or cyclic ones having 1 to 6 carbon atoms. Typical examples of the alkyl group may be methyl, ethyl, propyl, isopropyl, butyl, iso-butyl, sec.-butyl, tert.-butyl, pentyl, cyclopentyl, hexyl and cyclohexyl. Among them, for practical purposes, lower alkyl groups having 1 to 3 carbon atoms are preferred. The lower alkoxy group represented by the symbol R may be preferably that having 1 to 4 carbon atoms, such as methoxy, ethoxy, propoxy, isopropoxy, butoxy and isobutoxy. The acyloxy group represented by the symbol R may be lower alkyl carbonyloxy group whose alkyl moiety is that having 1 to 3 carbon atoms, and aryl carbonyloxy group. Typical examples of the acyloxy group may be acetoxy, propionyloxy, butyryloxy and benzoyloxy. The carboxy group R which may be esterified is represented by the formula —COOR', wherein R' represents hydrogen atom, lower alkyl group having 1 to 3 carbon atoms or aralkyl group. The lower alkyl group represented by the symbol R' is that having 1 to 3 carbon atoms, such as methyl, ethyl, propyl and isopropyl, and typical examples of the aralkyl group represented by the symbol R' may be benzyl, phenethyl. The alkyl substituted carboxamide group represented by the symbol R includes mono- or dialkyl substituted ones whose alkyl moiety is lower alkyl one having 1 to 3 carbon atoms and mono- or diaralkyl (e.g. benzyl) substituted ones. Typical examples of these groups may be N-methyl-carboxamide, N,N-dimethyl carboxamide, N-ethyl carboxamide, N,N-diethylcarboxamide, N-propyl carboxamide, N-benzyl carboxamide and N,N-dibenzyl carboxamide. The acyl-substituted amino group represented by the symbol R includes an amino group substituted by lower alkylcarbonyl group whose alkyl moiety is that having 1 to 3 carbon atoms and an amino group substituted by arylcarbonyl group. Typical examples of these group may be acetylamino, propionylamino, butyrylamino and benzoylamino. The hydrocarbon-substituted amino group represented by the symbol R includes mono- or di-lower alkyl substituted ones whose alkyl moiety is that having 1 to 3 carbon atoms, mono- or diaryl (e.g. phenyl, naphthyl) substituted ones and mono- or diaralkyl (e.g. benzyl, phenethyl) substituted ones. Typical examples of these groups may be methylamino, ethylamino, propylamino, isopropylamino, dimethylamino, diethylamino, dipropylamino, phenylamino, diphenylamino, benzylamino or phenethylamino. The halogen atom represented by the symbol R may be chlorine, bromine, iodine and fluorine.

In the present invention, the compounds of the general formula (I) are produced by reacting the compound (II)

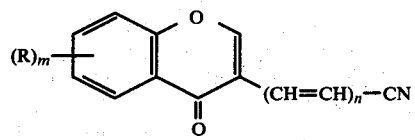

wherein R, m and n have the same meaning as defined above, with hydrazoic acid or a salt thereof.

The salt of hydrazoic acid employable in the present invention includes salts of hydrazoic acid with alkali metals or alkaline earth metals such as lithium azide, sodium azide, potassium azide, magnesium azide, calcium azide, barium azide and strontium azide; the salts of hydrazoic acid with other metals capable of forming salts with hydrazoic acid, such as, aluminum azide, tin azide, zinc azide and titanium azide; and the salts of hydrazoic acid with ammonia or organic amines (e.g. aniline, quinoline, imidazole).

In the reaction of the present invention, the salts of hydrazoic acid with alkali metals also can be employed in combination with, for example, a Lewis acid such as aluminum chloride, stannic chloride, zinc chloride or titanium tetrachloride or ammonium chloride.

The amount of hydrazoic acid, a salt thereof or the Lewis acid or its equivalent used in combination with the salt of hydrazoic acid is generally about 1 to 7 moles per mole of the starting compound (II) for practical purposes.

Generally, the reaction is desirably carried out in an organic solvent. The solvent is exemplified by hydrocarbons such as benzene, toluene, petroleum ether; ethers such as tetrahydrofuran, dioxane, ethyl ether and ethylene glycol dimethyl ether; dimethylformamide; formamide; dimethylsulfoxide. While the reaction conditions including temperature and time factors are largely optional, it is generally convenient to carry out the reaction at room temperature to about 150° C. for about 1 hour to about 2 days.

When a salt of hydrazoic acid is used as one of the starting compounds, the reaction of this invention yields the compound of the general formula (I) in the form of the salt corresponding to the hydrazoate used due to the acid function of the tetrazole ring. This salt, however, can be easily converted to the object compound (I) possessing a free tetrazole ring by treating it with a suitable acid (e.g. a mineral acid such as hydrochloric acid or sulfuric acid).

The compound of the general formula (I) which can be obtained in the foregoing manner can be isolated and purified by procedures which are conventional per se (e.g. extraction, chromatography, recrystallization, etc.).

When the compound of the general formula (I) is substituted by alkoxy or acyloxy group(s), these alkoxy and acyloxy groups can be converted to hydroxyl groups by procedures of conventional dealkylation or deacylation (e.g. hydrolysis with a hydrohalogenic acid such as hydrochloric acid, hydrobromic acid or hydroiodic acid and with a mineral acid such as sulfuric acid).

Moreover, when the compound of the general formula (I) is substituted by acylamino group(s), the acylamino group can be converted to amino group(s) under conditions similar to the above conditions of hydrolysis which are conventionally used for the cleavage of amide bonds. On the contrary, when the object compound of the general formula (I) is substituted by hydroxy, amino or carboxy group(s), these groups can be converted to acyloxy, acylamino, esterified carboxy or carboxamide group which may be substituted by conventional acylation, esterification or amidation. Further, when the object compound of the general formula (I) has a free tetrazole ring, it can be converted to an organic amine salt, alkali metal salt or ammonium salt by reacting the compound of the general formula (I) with an organic amine, e.g. ethanolamine, dl-methylephedrine, 1-(3,5-dihydroxyphenyl)-L-isopropylaminoethanol, isoproterenol, dextromethorphan, Hetrazan (diethylcarbamazine), diethylamine or triethylamine; an alkali metal hydroxide, e.g. sodium hydroxide or potassium hydroxide; alkali metal carbonate, e.g. sodium carbonate or potassium carbonate; or ammonia in a per se conventional manner, e.g. by admixing and heating the reactants together in the presence of an appropriate solvent (e.g. water, alcohol, dioxane, tetrahydrofuran).

The thus produced object compound (I) or their pharmaceutically acceptable salts, above all, the salts with the organic amines mentioned above specifically, have an effective anti-allergic action and are useful as medicines for allergic diseases such as allergic bronchial asthma, allergic dermatitis, allergic rhinitis and hay fever.

Further, since the alkali metal salts and organic amine salts of the compound (I) are highly soluble in water, and the solutions so formed are stable, they lend themselves well to manufacturing such pharmaceutical preparations as injections and solutions.

When the compounds of the general formula (I) or pharmaceutically acceptable salt thereof are employed as anti-allergic agents for treating or preventing the above-mentioned allergic diseases, these compounds are administered per se or in the form of a pharmaceutically acceptable composition in admixture with suitable and conventional carriers or adjuvants.

The pharmaceutical composition may take the form of tablets, capsules, granules, powders, solution, injections, ointments, sprays or aerosol inhalants, and can be administered orally or parenterally. Especially, the compounds of the present invention show effective action even upon oral administration, and therefore they are very advantageous from a practical point of view.

The usual daily doses of the present compounds lie in the range of about 1 to about 500 mg. more precisely of about 50 to 500 mg. upon oral administration and about 1 to about 200 mg. upon parenteral administration per adult human.

One of the starting compounds (II) of the present invention may be produced by, for example, the following procedure:

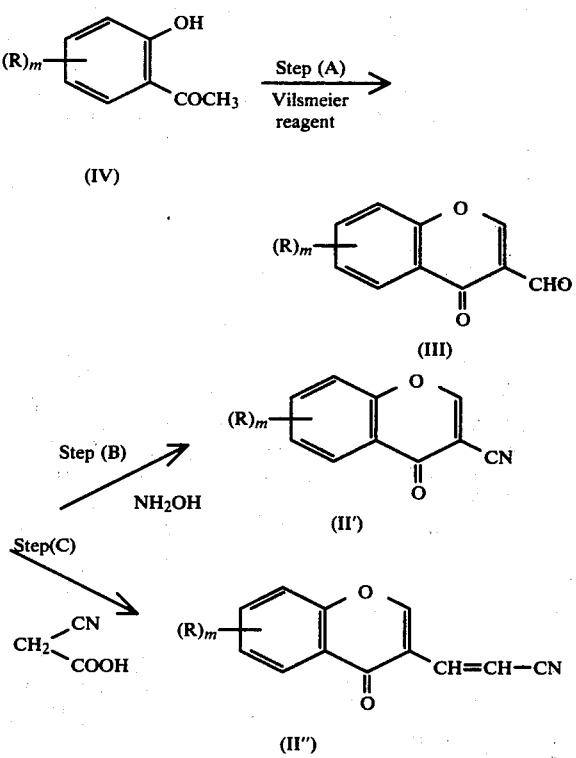

wherein R and m have the same meaning as defined above.

The reaction of the Step (A) is conducted by reacting a compound of the general formula (IV) with Vilsmeier reagent, which consists of equivalent mole(s) of dimethylformamide and acid chloride such as phosphorus oxychloride, tetrachloropyrophosphate, thionylchloride, phosgene, phosphorus pentachloride, etc., in the presence or absence of a suitable inert solvent. As the solvent, any solvent which does not restrict the reaction may be employed. Typical examples of the solvent are benzene, diethyl ether, petroleum benzine, chloroform or mixtures thereof.

The amount of the dimethylformamide and the acid chloride of Vilsmeier reagent is usually at least not less than 2 moles, preferably 10 to 12 moles per mole of a compound of the general formula (IV), respectively. The reaction can proceed at room temperature under atmospheric pressure, but, if necessary, may be carried out under heating up to the boiling point of dimethylformamide or of the solvent used or cooling down to −30° C. or under heating and elevated pressure. The reaction time varies with the reaction conditions such as temperature, pressure or kinds of acid chloride and solvent used, but is generally from 25 minutes to 24 hours.

The reaction of Step(B) is preferably conducted by reacting a compound of the general formula (III) with hydroxylamine in the presence of a suitable solvent such as alcohols (e.g. methanol, ethanol and prepanol) or ether (e.g. dioxane and tetrahydrofuran).

While hydroxylamine may be the free base, it is preferable to employ the corresponding hydrochloride. The amount of this reactant is usually about 1 to about 4 moles per mole of the compound (III).

The reaction conditions including the reaction temperature and time are largely optional, it is usually sufficient to conduct the reaction at 0° to 150° C. for 1 to 24 hours.

The reaction of Step(C) is conducted by reacting a compound of the general formula (III) with cyanoacetic acid in a solvent and in the presence of a base. The amount of cyanoacetic acid to be used in this reaction is usually about 1 to 2 moles per mole of the compound of the general formula (III).

The solvent is exemplified by hydrocarbons such as benzene, petroleum ether, etc.; ethers such as methyl ether, ethyl ether, etc., and alcohols such as methanol, ethanol, etc. The base is exemplified by tertiary amines such as trimethylamine, triethylamine, N-methylpiperidine, N-methylmorpholine, N-methylpyrrolidine, etc; heteroaromatic compound such as pyridine, 2-methylpyridine, 3methylpyridine, quinoline, 2-methylquinoline, imidazole, 2-methylimidazole, etc. Among these compounds, heteroaromatic compounds are the most desirable from all practical purposes. These bases may also be expected to function as the reaction solvent. The reaction conditions including the reaction temperature and time cannot be stated in general terms, for they depend upon the type of solvent and starting compounds to be used. Generally speaking, it is desirable to conduct the reaction at room temperature to a temperature near the boiling point of the solvent used, although one may conduct the reaction at a reduced temperature, if required. The reaction time is usually about several minutes to about 10 hours.

Incidentally, the above compound (IV) wherein R is amino group which may be substituted by alkyl group may be produced by, for example, the following procedures:

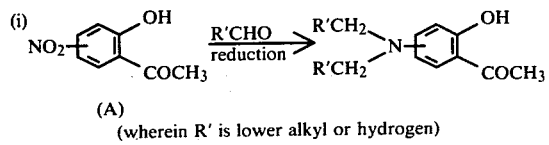

(A)

(wherein R' is lower alkyl or hydrogen)

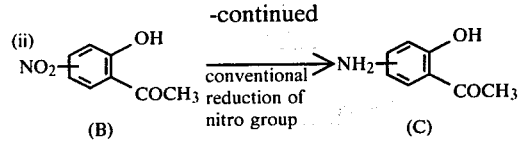

The above compound (IV) wherein R is amino group which is substituted by alkyl, aralkyl or acyl group may also be produced by reacting the compound (C) with conventional alkylating, aralkylating or acylating agent.

For example, the compound (IV) wherein R is dimethylamino group is produced as follows;

Into a mixture of 10 weight parts of 2-hydroxy-5-nitro-acetophenone in 200 volume parts of methanol and 22 volume parts of 37% aqueous formaldehyde solution is introduced at 25° C. 5500 volume parts of hydrogen in the presence of 2 weight parts of palladium-carbon catalyst and 5 volume parts of 2N-HCl. The resultant is filtered and concentrated to give 5-dimethylamino-2-hydroxyacetophenone as yellow needles melting at 75°–76.5° C.

For a further explanation of the present invention, the following Reference Examples and Examples are given, wherein the word "part(s)" is based on weight unless otherwise noted and the relationship between "part(s)" and "volume part(s)" corresponds to that between "gram(s)" and "milliliter(s)."

REFERENCE EXAMPLES

Reaction of Step(A)

In 80 volume parts of dimethylformamide are dissolved 25 parts of orthohydroxyacetophenone and, while the solution is externally cooled to about −20° C. with dry ice-acetone, 80 volume parts of tetrachloropyrophosphoric acid are added dropwise to the solution. The resulting mixture is stirred at room temperature for 13 hours. Then, the reaction mixture is poured into ice water and the resulting crystals are recovered by filtration, washed with water and ethanol and finally recrystallized from acetone. The procedure yields of 4-oxo-4H-1-benzopyran-3-carboxaldehyde as colorless crystals melting at 152°–153° C.

Analysis for $C_{10}H_6O_3$ Calcd. C, 68.96; H, 3.47; Found C, 68.70; H, 3.37.

When N-N-diethyl formaldehyde and N-phenyl N-methylformamide are respectively employed in place of dimethylformamide in the above procedure, 4-oxo-4H-1-benzopyran-3-carboxaldehyde are produced, respectively.

By the procedure similar to the above reference, the following compounds are synthesized.

| Starting materials | Product | Crystal form Recrystallization solvent | Melting point (° C.) |
|---|---|---|---|
| 2-Hydroxy-5-chloroacetophenone + Dimethylformamide | 6-Chloro-4-oxo-4H-1-benzopyran-3-carboxaldehyde | White scales | 166–168 |
| 2-Hydroxy-5-nitroacetophenone + Dimethylformamide | 6-Nitro-4-oxo-4H-1-benzopyran-3-carboxaldehyde | Pale yellow prisms Acetone | 163–164 |
| 2-Hydroxy-3,5-dimethyl acetophenone + Dimethylformamide | 6,8-Dimethyl-4-oxo-4H-1-benzopyran-3-carboxaldehyde | Colorless needles Dimethyl formamide + Acetone | 186–187 |

-continued

| Starting materials | Product | Crystal form Recrystallization solvent | Melting point (° C.) |
|---|---|---|---|
| 2-Hydroxy-3,5-dibromo acetophenone + Dimethylformamide | 6,8-Dibromo-4-oxo-4H-1-benzopyran-3-carboxaldehyde | Colorless needles | 177–178 |
| 2-Hydroxy-5-dimethyl aminoacetophenone + Dimethylformamide | 6-Dimethylamino-4-oxo-4H-1-benzopyran-3-carboxaldehyde | Yellow needles Dimethylformamide + Acetone | 153–154.5 |
| 2-Hydroxy-5-isopropyl acetophenone + Dimethylformamide | 6-Isopropyl-4-oxo-4H-1-benzopyran-3-carboxaldehyde | Yellow needles Ethylacetate + Petroleum ether | 98–99.5 |
| 2-Hydroxy-5-proylaceto-phenone + Dimethylformamide | 6-Propyl-4-oxo-4H-1-benzopyran-3-carboxyaldehyde | Pale yellow scales Ligroin + Ethylacetate | 100–102 |
| 2-Hydroxy-5-n-butyl-acetophenone + Dimethylformamide | 6-n-Butyl-4-oxo-4H-1-benzopyran-3-carboxaldehyde | Colorless needles Ligroin + Cyclohexane | 86.5–88.5 |
| 2-Hydroxy-5-methylacetophenone + Dimethylformamide | 6-methyl-4-oxo-4H-1-benzophran-3-carbox aldehyde | Colorless scales acetone | 174–175 |
| 2-Hydroxy-4-methoxy-acetophenone + Dimethylformamide | 7-Methoxy-4-oxo-4H-1-benzopyran-3-carbox-aldehyde | Pale yellow needles Acetone | 188–190 |
| 2-Hydroxy-5-methoxy-acetophenone + Dimethylformamide | 6-Methyoxy-4-oxo-4H-1-benzopyran-3-carbox-aldehyde | Pale yellow plates Acetone | 165–166 |
| 2-Hydroxy-6-methoxy-acetophenone + Dimethylformamide | 5-Methoxy-4-oxo-4H-1-benzopyran-3-carbox-aldehyde | Pale yellow plates Acetone | 115–116 |
| 2-Hydroxy-5-ethyl-acetophenone + Dimethylformamide | 6-Ethyl-4-oxo-4H-1-benzopyran-3-carboxaldehyde | Colorless scales Ethylacetate | 109–111 |
| 2-Hydroxo-6-acetoxy-acetophenone + Dimethylformamide | 5-Acetoxy-4-oxo-4H-1-benzopyran-3-carbox-aldehyde | Colorless needles Acetone | 174.5–176.5 |
| 2-Hydroxy-4-acetoxy-acetophenone + Dimethylformamide | 7-Acetoxy-4-oxo-4H-1-benzopyran-3-carbox-aldehyde | Pale yellow needles Acetone | 155–156 |
| 2-Hydroxy-5-carboxy-acetophenone + Dimethylformamide | 6-Carboxy-4-oxo-4H-1-benzopyran-3-carbox-aldehyde | Colorless crystals Acetone | 271.5–273.5 (decomp.) |
| 2,4-Dihydroxy-acetophenone + Dimethylformamide | 7-Hydroxy-4-oxo-4H-1-benzopyran-3-carbox-aldehyde | Yellow prisms DMF + Acetone + H₂O | 266.5–268.5 (decomp.) |
| 2-Hydroxy-5-acetamino-acetophenone + Dimethylformamide | 6-Acetamino-4-oxo-4H-1-benzopyran-3-carbox-aldehyde | Pale yellow powder Acetone | 231–233 |

REACTIONS OF STEP (B) AND (C)

Reference 1

2.52 Parts of 4-oxo-4H-1-benzopyran-3-carboxaldehyde are admixed well with 2.10 parts of hydroxylamine hydrochloride, followed by the addition of 30 volume parts of 95 weight % ethyl alcohol and 0.5 volume part of concentrated hydrochloric acid. The whole mixture is refluxed for 6 hours and cooled. The resulting precipitate is recovered by filtration, treated with activated carbon and recrystallized from ethanol. This procedure yields 4-oxo-4H-1-benzopyran-3-carbonitrile as colorless crystals. Melting point: 177°–178° C.

Analysis for $C_{10}H_5NO_2$ Calcd. C, 70.17; H, 2.95; N, 8.19; Found C, 70.00; H, 2.80; N, 8.13.

Reference 2

A mixture of 10.44 parts of 4-oxo-4H-1-benzopyran-3-carboxaldehyde and 5.4 parts of cyanoacetic acid are heated in an oil bath at 110° C., and to the mixture 25 volume parts of pyridine are added dropwise over about 30 seconds, after which time the whole mixture is further heated for 8 minutes. After cooling, the separated crystals are recovered by filtration, treated with activated carbon and recrystallized three times from ethanol. This procedure yields trans-3-(4-oxo-4H-1-benzopyran-3-yl)-acrylonitrile as pale-yellowish prisms. Melting point: 192°–194° C.

Analysis for $C_{12}H_7NO_2$ Calcd. C, 73.09; H, 3.58; N, 7.10; Found C, 73.48; H, 3.60; N, 7.01.

By procedures similar to the above procedure, the following compounds are synthesized.

| Starting compound | Product | Crystal form Recrystallization solvent | Melting point (° C.) |
|---|---|---|---|
| 6-Methyl-4-oxo-4H-1-benzopyran-3-carbox-aldehyde | 6-Methyl-4-oxo-4H-1-benzopyran-3-carbonitrile | Colorless needles Ethanol | 152.5–153.5 |
| 6-Ethyl-4-oxo-4H-1-benzopyran-3-carbox-aldehyde | 6-Ethyl-4-oxo-4H-1-benzopyran-3-carbonitrile | Colorless crystals Ethanol | 123–124 |
| 6-Chloro-4-oxo-4H-1-benzopyran-3-carbox-aldehyde | 6-Chloro-4-oxo-4H-1-benzopyran-3-carbonitrile | Yellow prisms Methanol | 210–213 |
| 6-Methoxy-4-oxo-4H-1-benzopyran-3-carbox-aldehyde | 6-Methoxy-4-oxo-4H-1-benzopyran-3-carbonitrile | Colorless needles Ethanol | 194–195 |
| 6-n-Hexyl-4-oxo-4H-1-benzopyran-3-carbox-aldehyde | 6-n-Hexyl-4-oxo-4H-1-benzopyran-3-carbonitrile | Colorless plates Ethanol-hexane | 55 |
| 7-n-Butoxy-4-oxo-4H-1-benzopyran-3-carbox-aldehyde | 7-n-Butoxy-4-oxo-4H-1-benzopyran-3-carbonitrile | Pale yellow plates Benzene-n-Hexane | 120–121 |
| 6-Dimethyl-amino-4-oxo-4H-1-benzopyran-3-carbox-aldehyde | 6-Dimethyl-amino-4-oxo-4H-1-benzopyran-3-carbonitrile | Yellow needles Chloroform-ethyl acetate | 167–168 |
| 3-Formyl-benzo(h)-chromone | 3-Cyanobenzo-(h)-chromone | Pale brown plates Acetone | 229–230 (decomp.) |

-continued

| Starting compound | Product | Crystal form Recrystallization solvent | Melting point (° C.) |
|---|---|---|---|
| 3-Formyl-benzo(f)-chromone | 3-Cyanobenzo-(f)-chromone | Colorless needles / Ethanol | 194.5–195.5 |
| 6-Cyclohexyl-4-oxo-4H-1-benzopyran-3-carboxaldehyde | 6-Cyclohexyl-4-oxo-4H-1-benzopyran-3-carbonitrile | Pale brown plates / Methanol | 164–165 |
| 6-n-Propyl-4-oxo-4H-1-benzopyran-3-carboxaldehyde | 6-n-Propyl-4-oxo-4H-1-benzopyran-3-carbonitrile | Pale yellow needles / Ethanol | 102–104 |
| 6-Isopropyl-4-oxo-4H-1-benzopyran-3-carboxaldehyde | 6-Isopropyl-4-oxo-4H-1-benzopyran-3-carbonitrile | Pale yellow needles / Ethanol | 118–120 |
| 7-Methoxy-4-oxo-4H-1-benzopyran-3-carboxaldehyde | 7-Methyoxy-4-oxo-4H-1-benzopyran-3-carbonitrile | Pale yellow needles / Methanol | 191–193 |
| 6-n-Butyl-4-oxo-4H-1-benzopyran-3-carboxaldehyde | 6-n-Butyl-4-oxo-4H-1-benzopyran-3-carbonitrile | Colorless needles / Ethanol | 94–95 |
| 6-n-Butyl-4-oxo-4H-1-benzopyran-3-carboxaldehyde | Trans-3-(6-n-Butyl-4-oxo-4H-1-benzopyran-3-yl)-acrylonitrile | Colorless needles / Ligroin-Benzene | 124–126 |
| 6-Nitro-4-oxo-4H-1-benzopyran-3-carboxaldehyde | 6-Nitro-4-oxo-4H-1-benzopyran-3-carbonitrile | Colorless plates / Methanol-Chloroform | 211–213 |
| 7-Acetoxy-4-oxo-4H-1-benzopyran-3-carboxaldehyde | 7-Hydroxy-4-oxo-4H-1-benzopyran-3-carbonitrile | Colorless needles / Ethanol | 278–280 |
| 6-Ethoxycarbonyl-4-oxo-4H-1-benzopyran-3-carboxaldehyde | 6-Ethoxycarbonyl-4-oxo-4H-1-benzopyran-3-carbonitrile | Colorless needles / Benzene | 164–165 |
| 6,8-Dimethyl-4-oxo-4H-1-benzopyran-3-carboxaldehyde | 6,8-Dimethyl-4-oxo-4H-1-benzopyran-3-carbonitrile | Colorless needles / Acetone | 196–198 |
| 7-Acetoxy-4-oxo-4H-1-benzopyran-3-carboxaldehyde | 7-Acetoxy-4-oxo-4H-1-benzopyran-3-carbonitrile | Colorless hairly crystals / Ethanol | 182–183 (decomp.) |
| 7-Benzoyloxy-4-oxo-4H-1-benzopyran-3-carboxaldehyde | 7-Benzoyloxy-4-oxo-4H-1-benzopyran-3-carbonitrile | Plates / Ethanol-tetrahydrofuran | 200–202 |
| 6,7-Dihydroxy-4-oxo-4H-1-benzopyran-3-carboxaldehyde | 6,7-Dihydroxy-4-oxo-4H-1-benzopyran-3-carbonitrile | Pale brown powder / Dimethylformamide-water | higher than 300 |

EXAMPLES

Example 1

To 100 volume parts of dry tetrahydrofuran are added 4.28 parts of comminuted anhydrous aluminum chloride, 2.50 parts of 4-oxo-4H-1-benzopyran-3-carbonitrile and 4.18 parts of sodium azide in this order and, the whole mixture is refluxed under stirring for 23 hours. Then, to the resulting mixture 35 volume parts of 15 weight% hydrochloric acid are added, followed by distilling off tetrahydrofuran under reduced pressure. The resulting solid residue is recovered by filtration and recrystallized from dimethylformamide. This procedure yields 3-(1H-tetrazol-5-yl) chromone as colorless hairy needles. Melting point: 284°–285° C.(decomp. with foaming).

Analysis for $C_{10}H_6N_4O_2$ Calcd. C, 56.07; H, 2.82; N, 26.16; Found C, 56.16; H, 2.60; N, 26.27.

EXAMPLE 2

Under stirring, 4.6 parts of anhydrous aluminum chloride are added to 100 volume parts of dry tetrahydrofuran, followed by the addition of 3.11 parts of trans-3-(4-oxo-4H-1-benzopyran-3-yl)-acrylonitrile and 4.5 parts of sodium azide. The whole mixture is refluxed for 28 hours and, then, 35 volume parts of 15 weight% hydrochloric acid are added to the resulting mixture, followed by distilling off tetrahydrofuran under reduced pressure. The resulting residue is recovered by filtration and recrystallized from methanol, dimethylformamide-water and, then, from methanol. This procedure yields trans-1-(4-oxo-4H-1-benzopyran-3-yl)-2-(1H-tetrazol-5-yl) ethylene as light-yellow needles. Melting point: 254.5°–255° C.(decomp. with foaming).

Analysis for $C_{12}H_8N_4O_2$ Calcd. C, 60.00; H, 3.36; N, 23.32; Found C, 59.98; H, 3.25; N, 23.15.

Mass spectrum: m/e 240(M+), 212, 196.

By procedures similar to the procedure described above, the following compounds are synthesized.

| Starting compound | Product | Crystal form Recrystallization solvent | Melting point (° C.) |
|---|---|---|---|
| 6-Methyl-4-oxo-4H-1-benzopyran-3-carbonitrile | 3-(1H-Tetrazol-5-yl)-6-methyl-chromone | Colorless scales / Dimethylformamide | 258–259 (decomp.) |
| 6-Ethyl-4-oxo-4H-1-benzopyran-3-carbonitrile | 3-(1H-Tetrazol-5-yl)-6-ethyl-chromone | Colorless needles / Dimethylformamide-water | 217–218 |
| 6-Chloro-4-oxo-4H-1-benzopyran-3-carbonitrile | 3-(1H-Tetrazol-5-yl)-6-chloro-chromone | Colorless needles / Dimethylformamide-water | 267.5 (decomp.) |
| 6-Methoxy-4-oxo-4H-1-benzopyran-3-carbonitrile | 3-(1H-Tetrazol-5-yl)-6-methoxy-chromone | Colorless hairy needles / Dimethylformamide-water | 281–282 (decomp. with foaming) |
| 6-n-Hexyl-4-oxo-4H-1-benzopyran-3-carbonitrile | 3-(1H-Tetrazol-5-yl)-6-n-hexyl-chromone | Colorless plates / Dimethylformamide-methanol | 207–210 |
| 7-n-Butoxy-4-oxo-4H-1-benzopyran-3-carbonitrile | 3-(1H-Tetrazol-5-yl)-7-n-butoxy-chromone | Colorless colum / Dimethylformamide-acetone | 236–238 (decomp. with foaming) |
| 6-Dimethylamino-4-oxo-4H-1-benzopyran-3-carbonitrile | 3-(1H-Tetrazol-5-yl)-6-dimethyl-aminochromone | Orange crystall powder / Dimethylformamide-acetone | 303–305 (decomp. with foaming) |

-continued

| Starting compound | Product | Crystal form Recrystallization solvent | Melting point (° C.) |
|---|---|---|---|
| 3-Cyanobenzo(h)chromone | 3-(1H-Tetrazol-5-yl)-benzo(h)-chromone | Pale brown rhombous Dimethylformamide-water | 303–305 (decomp. with foaming) |
| 3-Cyanobenzo(f)chromone | 3-(1H-Tetrazol-5-yl)-benzo(f)-chromone | Colorless prisms Dimethylformamide-water | 282–285 (decomp. with foaming) |
| 6-Cyclohexyl-4-oxo-4H-1-benzopyran-3-carbonitrile | 3-(1H-Tetrazol-5-yl)-6-cyclohexyl-chromone | Colorless needles Methanol-tetrahydrofuran | 252–253 |
| 6-n-Propyl-4-oxo-4H-1-benzopyran-3-carbonitrile | 3-(1H-Tetrazol-5-yl)-6-n-propyl-chromone | Colorless needles Dimethylformamide-methanol | 214–215 |
| 6-iso-Propyl-4-oxo-4H-1-benzopyran-3-carbonitrile | 3-(1H-Tetrazol-5-yl)-6-iso-propyl-chromone | Colorless needles Dimethylformamide-methanol | 222–223 |
| 7-Methoxy-4-oxo-4H-1-benzopyran-3-carbonitrile | 3-(1H-Tetrazol-5-yl)-7-methoxy-chromone | Colorless prisms Dimethylformamide | 277–279 |
| 6-n-Butyl-4-oxo-4H-1-benzopyran-3-carbonitrile | 3-(1H-Tetrazol-5-yl)-6-n-butyl-chromone | Colorless needles Dimethylformamide-methanol | 206–209 |
| Trans-3-(6-n-Butyl-4-oxo-4H-1-benzopyran-3)-acrylontrile | Trans-1-(6-n-butyl-4-oxo-1-benzopyran-3-yl)-2-(1H-tetrazol-5-yl)ethylene | Pale yellow fine needles Dimethylformamide-acetone | 247.5–250 |
| 6-Nitro-4-oxo-4H-1-benzopyran-3-carbonitrile | 3-(1H-Tetrazol-5-yl)-6-nitrochromone | Colorless needles Dimethylformamide | 285–286 (decomp. with foaming) |
| 7-Hydroxy-4-oxo-4H-1-benzopyran-3-carbonitrile | 3-(1H-Tetrazol-5-yl)-7-hydroxy-chromone | Colorless needles Dimethylformamide-water | higher than 300 |
| 6-Amino-4-oxo-4H-1-benzopyran-3-carbonitrile | 3-(1H-Tetrazol-5-yl)-6-aminochromone | Reddish-yellow plate Dimethylformamide-water | higher than 300 |
| 6-Ethoxycarbonyl-4-oxo-4H-1-benzopyran-3-carbonitrile | 3-(1H-Tetrazol-5-yl)-6-ethoxycarbonyl-chromone | Colorless needles Dimethylformamide-acetone | 271–273 (decomp. with foaming) |
| 6,8-Dimethyl-4-oxo-4H-1-benzopyran-3-carbonitrile | 3-(1H-Tetrazol-5-yl)-6,8-dimethyl-chromone | Colorless needles Dimethylformamide | 274–275 (decomp. with foaming) |
| 7-Acetoxy-4-oxo-4H-1-benzopyran-3-carbonitrile | 3-(1H-Tetrazol-5-yl)-7-acetoxy-chromone | Colorless micro crystals Dimethylformamide | 247–248 (decomp. with foaming) |
| 7-Benzoyloxy-4-oxo-4H-1-benzopyran-3-carbonitrile | 3-(1H-Tetrazol-5-yl)-7-benzoyloxy-chromone | Colorless plates Dimethylformamide-ethanol | 243–245 |
| 6,7-Dihydroxy-4-oxo-4H-1-benzopyran-3-carbonitrile | 3-(1H-Tetrazol-5-yl)-6,7-dihydroxy-chromone | Colorless needles Dimethylformamide-water | higher than 300 |

EXAMPLE 3

To 140 parts of aquous solution containing 8 parts of sodium carbonate, 20 parts of 3-(1H-tetrazol-5-yl)-6-ethylchromone are added, and followed by heating. After cooling, insoluble portion is removed by filtration and the resulting mother liquid is cooled. This procedure gives sodium 3-(1H-tetrazol-5-yl)-6-ethylchromon as pale yellow crystal melting at 286°–288° C. (decomp.)

Analysis for $C_{12}H_9N_4O_2Na \cdot 2H_2O$ Calcd. C, 48.00; H, 4.36; N, 18.66; Found C, 48.02; H, 4.46; N, 18.76.

EXAMPLE 4

0.112 Part of 3-(1H-tetrazol-5-yl)-6-ethylchromone and 0.0895 part of DL-methylephedrine are added to 5 parts of ethanol under stirring. The resulting solution is concentrated to dryness, and the precipitated residue is recrystallized from 2 parts of ethanol. This procedure gives 3-(1H-tetrazol-5-yl)-6-ethylchromone DL-methylephedrine salt as colorless plates melting at 172° C.

Analysis for $C_{23}H_{27}O_3N_5$ Calcd. C, 65.53; H, 6.45; N, 16.61; Found C, 65.79; H, 6.52; N, 16.44.

By a procedure similar to that described above, the following compounds are obtained.

| Starting compound | Product | Crystal form Recrystallization solvent | Melting point (° C.) |
|---|---|---|---|
| 3-(1H-Tetrazol-5-yl)-6-ethylchromone + Diethanolamine | Diethanolamine salt | Colorless plates Ethanol | 150 |
| 3-(1H-Tetrazol-5-yl)-6-ethylchromone + Monoethanolamine | Monoethanolamine salt | Colorless needles Ethanol | 152 |
| 3-(1H-Tetrazol-5-yl)-6-ethylchromone + Diethylamine | Diethylamine salt | Colorless scales Ethanol-ethylether | 223 |

EXAMPLE 5

0.244 Part of 3-(1H-tetrazol-5-yl)-6-methoxychromone is added to 8 parts of 57 weight % hydrojodic acid, and the whole mixture is heated at 140° C. for 2 hours.

Resulting insoluble portion is collected by filtration and recrystallized from dimethyl formamide-water, whereby 3-(1H-tetrazol-5-yl)-6-hydroxychromone is obtained as colorless needles melting at higher than 300° C.

Analysis for $C_{10}H_6N_4O_3$ Calcd. C, 52.18; H, 2.63; N, 24.34; Found C, 51.81; H, 2.68; N, 24.16.

I.R. spectrum (KBr)cm$^{-1}$: 1635, 1610, 1588 (chromone), 1540.

N.M.R. spectrum (d$_6$-DMSO) δ: 10.5(1H, broad, OH), 9.25 (1H, singlet, C$_2$-H), 7.2–7.8(3H, multiplet).

EXAMPLE 6

Some examples of practical recipes in which the compounds of this invention are utilized as remedies for an allergic disease are as follows:

A.(Tablet)

| | |
|---|---|
| (1) 3-(1H-tetrazol-5-yl)-6-ethylchromone | 20 mg. |
| (2) lactose | 35 mg. |
| (3) corn starch | 150 mg. |
| (4) microcrystalline cellulose | 30 mg. |
| (5) magnesium stearate | 5 mg. |
| | 240 mg. per tablet |

(1), (2), (3), ⅔ quantity of (4) and half quantity of (5) are throughly mixed, and then the mixture is granulated. Remaining ⅓ quantity of (4) and half of (5) are added to the granules and compressed into tablets. Thus prepared tablets can further be coated with a suitable coating agent, e.g. sugar.

B.(Capsule)

| | |
|---|---|
| (1) 3-(1H-tetrazol-5-yl)-6-ethylchromone | 20 mg. |
| (2) lactose | 102 mg. |
| (3) microcrystalline cellulose | 70 mg. |
| (4) magnesium stearate | 8 mg. |
| | 200 mg. per capsule |

(1), (2), (3) and half quantity of (4) are throughly mixed, and then the mixture is granulated. Remaining half of (4) is added to the granules and the whole is filled into a gelatin capsule.

C.(Injection)

| | |
|---|---|
| (1) sodium 3-(1H-tetrazol-5-yl)-6-ethylchromone | 10 mg. |
| (2) inositol | 100 mg. |
| (3) benzyl alcohol | 20 mg. |

All ingredients are dissolved in water to make 2.0 ml. of the solution (pH 7.5) serving as injection.

We claim:

1. A compound of the formula

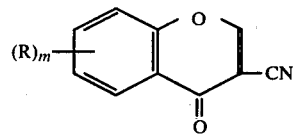

wherein m is 2 and each R when taken alone represents straight or branched alkyl up to 6 carbon atoms or when taken together represent butadienylene (—CH=CH—CH=CH—) which forms a benzene ring with any two adjacent carbon atoms at positions 5, 6, 7 and 8.

2. A compound as claimed in claim 1, wherein R represents straight chain alkyl up to 6 carbon atoms.

3. A compound as claimed in claim 1, wherein the R's when taken together represent butadienylene which forms a benzene ring with any two adjacent carbon atoms at positions 5, 6, 7 and 8.

4. A compound of the formula

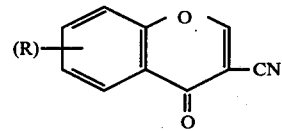

wherein m is 1 and R represents 6-halogen.

5. The compound 6-methoxy-4-oxo-4H-1-benzopyran-3-carbonitrile.

6. The compound 7-methoxy-4-oxo-4H-1-benzopyran-3-carbonitrile.

7. The compound according to claim 2 which is 6,8-dimethyl-4-oxo-4H-1-benzopyran-3-carbonitrile.

8. The compound according to claim 3 which is 3-cyanobenzo[h]chromone.

9. The compound according to claim 3 which is 3-cyanobenzo[f]chromone.

10. The compound according to claim 4 which is 6-chloro-4-oxo-4H-1-benzopyran-3-carbonitrile.

* * * * *